(12) United States Patent
Kaneko et al.

(10) Patent No.: US 7,194,896 B2
(45) Date of Patent: Mar. 27, 2007

(54) SURFACE HARDNESS DISTRIBUTION MEASURING METHOD AND APPARATUS

(75) Inventors: Makoto Kaneko, Higashihiroshima (JP); Shinji Tanaka, Hiroshima (JP); Tomohiro Kawahara, Higashihiroshima (JP); Shinji Takeuchi, Saitama (JP)

(73) Assignees: Makoto Kaneko and Tomohiro Kawahara, Higashihiroshima (JP); Fujinon Corporation, Saitama (JP); Shinji Tanaka, Hiroshima (JP)

( * ) Notice: Subject to any disclaimer, the term of this patent is extended or adjusted under 35 U.S.C. 154(b) by 174 days.

(21) Appl. No.: 10/940,731

(22) Filed: Sep. 15, 2004

(65) Prior Publication Data

US 2005/0061062 A1    Mar. 24, 2005

(30) Foreign Application Priority Data

Sep. 19, 2003   (JP) .............................. 2003-327638

(51) Int. Cl.
    *G01N 3/48* (2006.01)
(52) U.S. Cl. ......................................................... 73/81
(58) Field of Classification Search ................... 73/78, 73/81–84; 356/625, 626; 600/306
    See application file for complete search history.

(56) References Cited

U.S. PATENT DOCUMENTS 3,838,428 A * 9/1974 Benson et al. ............ 346/33 R
4,275,966 A * 6/1981 Kleesattel ................... 356/626
4,817,883 A * 4/1989 Hoffmann et al. .......... 242/534
5,146,779 A * 9/1992 Sugimoto et al. .............. 73/81
5,282,382 A * 2/1994 Fiore et al. ..................... 73/82
6,755,075 B2 * 6/2004 Nagashima et al. .......... 73/105

FOREIGN PATENT DOCUMENTS

JP     59-069722     4/1984
JP     2003-235785   8/2003

* cited by examiner

*Primary Examiner*—Robert Raevis
(74) *Attorney, Agent, or Firm*—Snider & Associates; Ronald R. Snider

(57) ABSTRACT

It is possible to blast air on a surface portion of a measured object from a hole of pressing means, project illumination light in a concentric pattern with an optical element and shoot the measured object with a CCD so as to visually grasp hardness distribution on the surface portion from distortion of the concentric pattern displayed on an observed image. As for the hardness distribution, it is possible to detect luminance distribution of a measured object image obtained by the CCD so as to display the concentric pattern which is the luminance distribution as a conspicuous representation of the hardness distribution. And the luminance distribution can also be represented in the concentric pattern by multiplying a luminance value by an overflowing coefficient.

10 Claims, 7 Drawing Sheets

PRIOR ART

SURFACE HARDNESS DISTRIBUTION MEASURING METHOD AND APPARATUS

BACKGROUND OF THE INVENTION

The application claims the priority of Japanese Patent Applications No. 2003-327638 filed on Sep. 19, 2003 which is incorporated herein by reference.

1. Field of the Invention

The present invention relates to a surface hardness distribution measuring method and an apparatus thereof, and in particular, to the surface hardness distribution measuring method and apparatus capable of measuring hardness distribution of a surface portion of a farm product and a tissue surface portion in a medical field in one or more dimensions and visually grasping the hardness distribution.

2. Description of the Related Art

There are ongoing researches for associating measurement of one's skin age, detection of a focus and detection of ripeness of vegetables and fruits with impedance parameters. In the case where a subject is a living bowel, there is no definite fixed point and so absolute measurement is difficult. If considered from a standpoint of finding a cancerous tissue for instance, however, it becomes a beneficial food for thought as regards a substantive diagnosis if relative hardness can be clarified in relation to surroundings. So far, there has been an air blast apparatus of an endoscope indicated in Japanese Patent Laid-Open No. 2003-235785, for instance, as the one for detecting a local hardness of living bowel linings.

Figure 13:
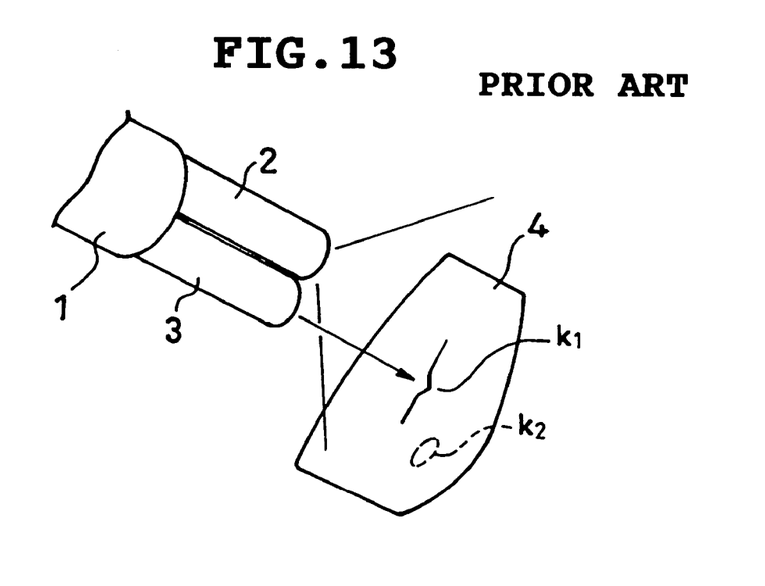
FIG. 13 is a perspective view showing a state of using an air blast apparatus of the endoscope in the past.

FIG. 13 shows a state of using such an apparatus. In FIG. 13, an endoscope end portion 1 has an optical objective portion 2 and an air blast probe 3 connected to an air supply apparatus provided thereto, where pulse-like pressurized air can be blasted from the air blast probe 3. It is possible, with such an endoscope, to blast the air from the air blast probe 3 to a stomach wall 4 (dotted area $k_1$) like pulses and optically observe a deformation and change state of the stomach wall 4 with an eye piece or a monitor via the optical objective portion 2 so as to grasp rigidity (hardness), viscosity and so on of the stomach wall 4.

SUMMARY OF THE INVENTION

As for the air blast apparatus of an endoscope in FIG. 13, however, an area of an air-blasted region is observed with an eye piece or a monitor, and so it is difficult to grasp hardness of a surface portion. Therefore, there is a problem that it is difficult to grasp it in the case where a deformation and change state of the surface is very little although it is not difficult in the case where the deformation and change state of the surface is comparatively conspicuous. There is also a problem that it can only grasp the hardness in a small range centering on a dotted area $k_1$ and it takes time to grasp and detect the hardness in a wide range in which a hard area $k_2$ exists, for example.

The present invention has been implemented in consideration of the above problems, and an object thereof is to provide a surface hardness distribution measuring method and an apparatus thereof capable of conspicuously representing a state of small deformations and changes on the surface portion and grasping or detecting hardness distribution of a measured object in a wide range visually, easily and in a short time.

To attain the above object, the surface hardness distribution measuring method according to the present invention is characterized by including a pressing step of exerting a force on the surface portion of the measured object with pressing means and a hardness distribution representing step of performing visual representation for visually (and conspicuously) observing hardness distribution of the measured object on exerting the force in the pressing step.

And the invention of another configuration comprises pressing means for exerting the force on the surface portion of the measured object, hardness distribution representing means for performing the visual representation for visually observing the hardness distribution of the measured object on exerting the force with the pressing means, and observing means for observing the measured object visually represented by the hardness distribution representing means.

Furthermore, the invention of a further configuration comprises the pressing means for exerting the force on the surface portion of the measured object, hardness detecting means for detecting the hardness distribution of the measured object on exerting the force with the pressing means in one or more dimensions, and a display portion for displaying the hardness distribution in one or more dimensions detected by the hardness detecting means.

It is possible to provide pattern projecting means for projecting a form pattern on the measured object as the hardness distribution representing means according to the invention, and also provide a shooting portion for, as the observing means, shooting the measured object which has the form pattern projected on by the pattern projecting portion and the force exerted on by the pressing means, and the display portion for displaying an image of the measured object shot by the shooting portion.

According to the configuration, for instance, the air or liquid is blasted or sprayed or the force is applied with a stick and so on to the surface portion of the measured object by the pressing means, and the form pattern (design) which is concentric, lattice-like (netted), straight-line or parallel-line is projected on the measured object. In this case, the surface portion of the measured object having external pressure exerted thereto deforms as if caving in (sagging). If there are variations in the hardness of the surface portion, however, the variations appear as distortions of the form pattern. Therefore, it is possible to observe the distortions of the form pattern with the observing means so as to easily detect and grasp the hardness distribution of the surface portion. The pressing means may either continuously provide a fixed pressure or provide a pulse-like pressure at a predetermined oscillation frequency.

The invention of a still further configuration has shooting means, as the observing means, for shooting the measured object on which the force is exerted by the pressing means and the display portion for displaying the image of the measured object shot by the shooting portion provided thereto, and also has a luminance distribution detecting circuit, as the hardness distribution representing means, for detecting luminance distribution of a measured object image obtained by the shooting means, and the display portion can display the luminance distribution obtained by the luminance distribution detecting circuit.

To be more specific, the hardness distribution is detected by means of the luminance distribution of the measured object image obtained by the shooting means. Considering the case of performing the process for rendering intensity distribution of illumination light constant (the case of illumination of even illuminance), the luminance lowers according to a distance from an illumination portion on a surface of an uneven measured object so that the luminance changes according to deformation. Therefore, if the distribution of the same luminance as to an imaged picture signal is acquired for a plurality of luminances, it is possible to display the distribution concentrically (like circular stripes) so as to visually (and conspicuously) grasp the hardness distribution according to a degree of the distortion of the concentric circles. It is also possible to conspicuously represent the luminance distribution in a concentric pattern by multiplying a luminance signal (digital signal) of the picture signal by a large coefficient exceeding a maximum luminance and generating an overflow status. In this case, it is also possible, as with the above, to visually grasp the hardness distribution according to the degree of the distortion of the concentric circles.

According to the surface hardness distribution measuring method and apparatus of the present invention, it is possible, for instance, to conspicuously represent the statuses of small deformations and changes by projecting the form pattern and detecting the luminance distribution so as to visually grasp the hardness of the measured object. It is also possible to perform the projection of the form pattern and detection of the luminance distribution in one dimension (line) or two dimensions (surface) rather than in dots so as to grasp the hardness distribution of the measured object in the wide range easily and in a short time. There is also an advantage that a value of the hardness is detectable by means of the hardness distribution of the measured object and so useful information on the hardness can be provided.

BRIEF DESCRIPTION OF THE DRAWINGS

FIGS. 6A and 6B show the configurations of form patterns projected by the apparatus of the second embodiment, where

FIGS. 7A and 7B show changes of the form patterns projected by the apparatus of the second embodiment, where

FIGS. 9A to 9C show appearances of luminance distribution detection performed in the third embodiment, where

FIGS. 10A to 10C show appearances of the luminance distribution detection performed in the fourth embodiment, where

DETAILED DESCRIPTION OF THE PREFERRED EMBODIMENTS

Figure 1A:
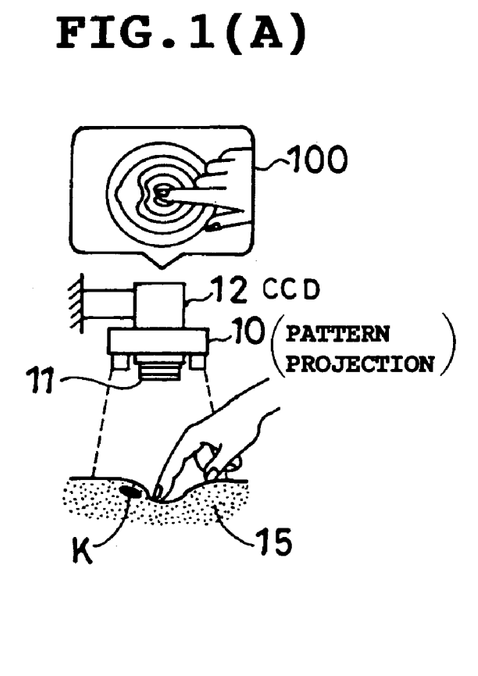
FIGS. 1A and 1B are block diagrams showing a principle of a surface hardness distribution measuring apparatus according to the present invention.
Figure 1B:
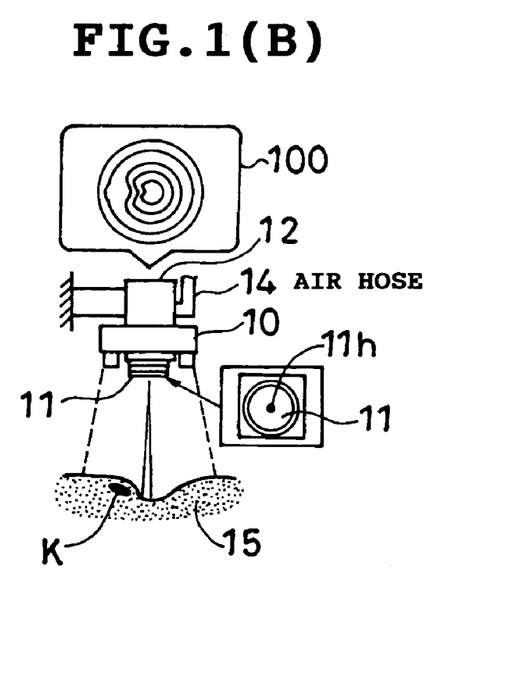

FIG. 1 shows a basic concept of the present invention. For instance, an optical member 10 for projecting illumination light in a concentric pattern and a CCD (Charge Coupled Device) 12 which is a solid-state imaging device for imaging a measured object via a lens 11 are provided. And as in FIG. 1B, it is constituted to be able to blast air toward the measured object via a hole 11$h$ at the center of the lens 11 and an air hose 14.

In FIG. 1A, in the case where a surface of the measured object is pushed by a fingertip after irradiating a concentric light pattern, if hardness distribution of the measured object is uniform, the form of the circle itself does not change even though spacing of the concentric circles may change due to deformation of the pushed portion. However, if a portion K harder than the surroundings exists in a measured object 15 in FIG. 1, the hardness distribution is no longer uniform so that the form of the circle gets distorted as shown in an observation image 100 on the upside of the drawing. It is possible to visually determine the hardness distribution from the form of the distortion. To be more specific, it is an impedance imager for measuring hardness relative to the surroundings, that is, relative impedance distribution in other words.

Here, if the finger is used as in FIG. 1A, a part of a perspective is hidden and a dead angle is made. Therefore, the hardness of the measured object can be measured well by blasting the air from a hole 11$h$ and exerting a force by the air blast as in FIG. 1B.

First Embodiment

Figure 2:
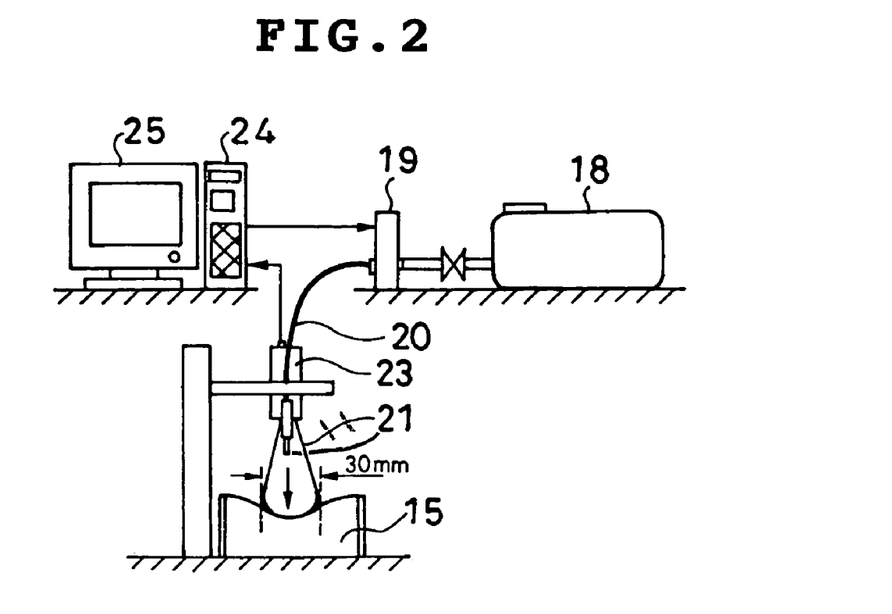
FIG. 2 is a diagram showing a configuration of the surface hardness distribution measuring apparatus according to a first embodiment.
Figure 3:
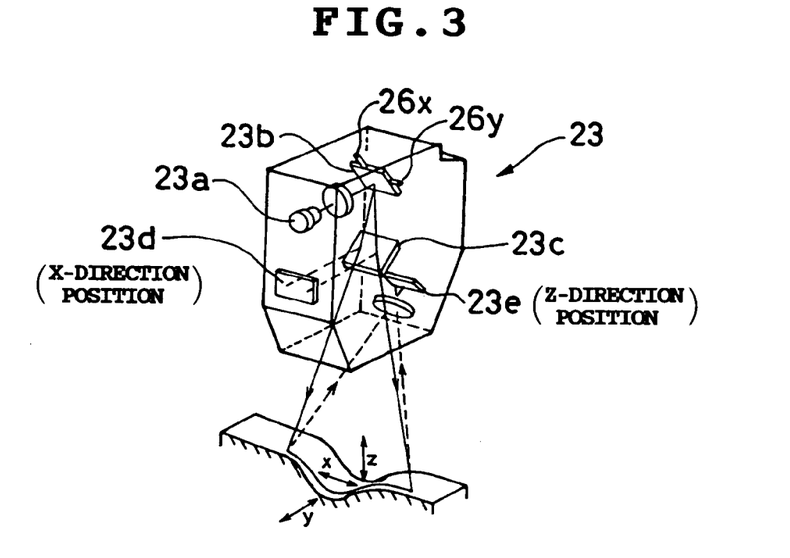
FIG. 3 is a perspective view showing the configuration of a line laser sensor of the apparatus according to the first embodiment.

FIGS. 2 and 3 show a configuration of the surface hardness distribution measuring apparatus according to a first embodiment. In the first embodiment in FIG. 2, an air compressor 18, a valve (solenoid valve) 19, an air hose 20 and a nozzle 21 for blasting (jet orifice: 2 mm or so) are provided as pressing means, and a line laser sensor 23 for detecting the hardness (a dent depth position) on a straight line of a measurement area (one dimension) based on the air blast is provided as hardness detecting means. In addition, a computer (a personal computer for instance) 24 for inputting an output of the line laser sensor 23 and performing a calculation for defining the hardness distribution of the measurement area as a graphic and a monitor 25 for displaying a graph for showing the hardness distribution and the graphs in one or more dimensions are provided. Although not shown, it is possible to provide the CCD for imaging the measured object 15 and display an image thereof on the monitor 25.

FIG. 3 shows the detailed configuration of the line laser sensor 23. The line laser sensor 23 has a laser output portion 23$a$ for generating a laser beam, a scanner (mirror) 23$b$ for rotating on rotation axes 26$x$ and 26$y$, a half mirror 23$c$, an X-direction position detecting portion 23$d$ for detecting a position in an x direction in the drawing, a Z-direction position detecting portion 23$e$ for detecting a position (distance) in a z direction (depth direction) and so on provided thereon. Such a line laser sensor 23 scans (one-dimensional scan) the laser beam 30 mm or so in the x direction in the drawing based on the rotation of the scanner 23b centering on the rotation axis 26x. The position of the laser beam in the x direction is detected by the X-direction position detecting portion 23d, and the position of the laser reflected beam in the z direction is detected by the Z-direction position detecting portion 23e. It can also scan the laser beam in the y direction in the drawing based on rotation of the scanner 23b centering on the rotation axis 26y so that a surface (two-dimensional) area can be scanned and detected.

FIG. 4 show results of hardness measurement in the first embodiment. In this measurement, a container 27 shown in FIG. 4A is evenly stuffed with absorbent cotton 28, and a constant pressure P is applied by the air blast to the measured object of which surface is covered with a stretch fabric. The air blast is given from a distance of 20 to 30 mm, for example, and the range of the air hitting the measured object is a diameter of 10 mm or so. FIG. 4B shows the results of the measurement in this case, where displacements to the right and left from the center of blast pressure are almost the same and it is symmetrically deformed. As in FIG. 4C, if it is measured by putting a glass bubble (2 mm) under the surface 10 mm away from the center of blast pressure P, symmetry of a displacement pattern is lost and the displacement on the left side from the center becomes extremely small as shown in the measurement results in FIG. 4D. Thus, it is possible to grasp and observe the hardness distribution of the surface portion of the measured object from this state.

Figure 4A:
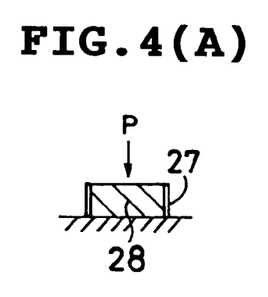
FIGS. 4A to 4D are graph charts showing hardness distribution measurement results obtained by the line laser sensor of the first embodiment.
Figure 4B:
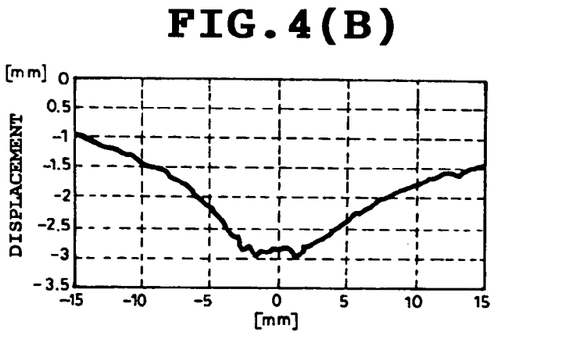
Figure 4C:
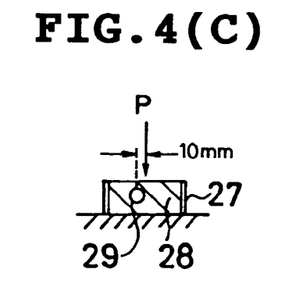
Figure 4D:
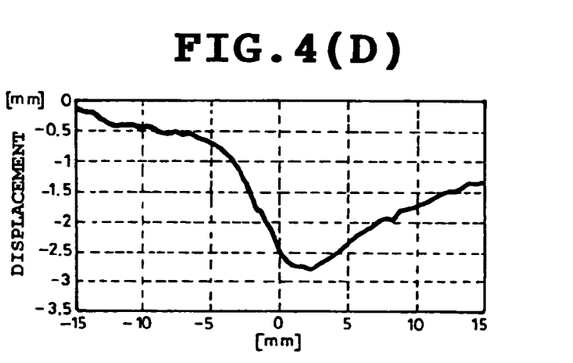

The graphs of the hardness distribution in FIGS. 4B and 4D are formed by the computer 24 and displayed on the monitor 25. According to such a display of the hardness distribution, it is possible to determine size and so on of a hard portion (glass bubble 29 here) existing under the measured object. And as described above, it is possible to detect the hardness distribution in a surface direction by repeating the scan in the x direction while gradually moving toward the y-axis direction, and the hardness distribution in the surface direction is also displayed on the monitor 25. It is possible, by the display in the surface direction, to three-dimensionally represent the form of the surface portion of the measured object pressed by the air so as to grasp and observe the hardness distribution in the wide range at a glance.

It is also possible to estimate an impedance parameter of the measured object on the air blast and evaluate the hardness. To be more specific, behavior of the measured object on applying the air blast is modeled (linear model) by the following formula 1 so as to estimate the impedance parameter.

$$m\ddot{x}+c\dot{x}+kx=f(t) [\dot{x}:\text{speed}, \ddot{x}:\text{acceleration}]$$ Formula 1

Here, x is displacement time-series data $[x_1, x_2, \ldots, x_n]^T$ on the measured object on applying the air blast. In addition, m represents mass, c represents viscosity, and k represents elasticity as parameters, and they are estimated to evaluate the hardness comprehensively.

Second Embodiment

Figure 5:
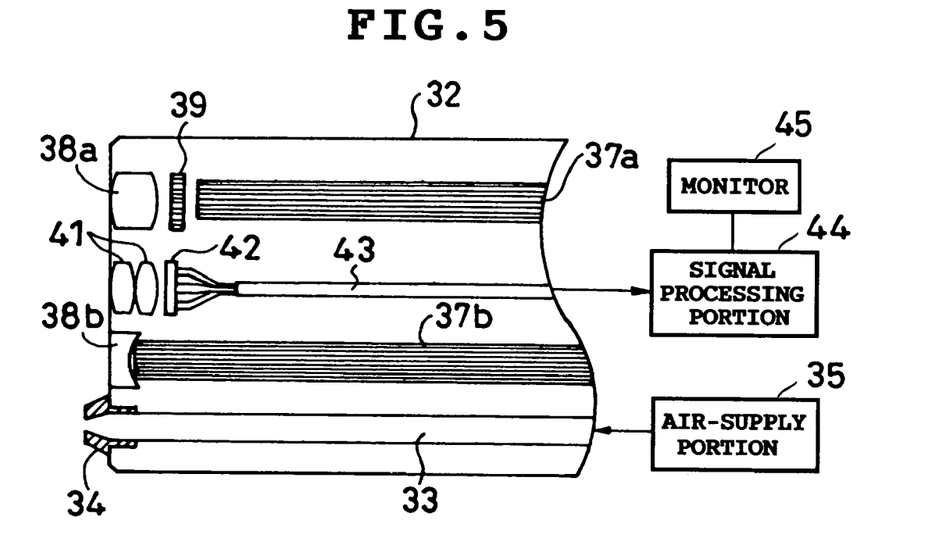
FIG. 5 is a diagram showing the configuration of the surface hardness distribution measuring apparatus for an endoscope according to a second embodiment.

FIG. 5 shows the configuration of the second embodiment in which the present invention is applied to an endoscope apparatus. As shown in FIG. 5, according to the second embodiment, an air-pipe 33 for supplying the air and a nozzle 34 are provided to an endoscope end portion 32. The air-pipe 33 is coupled to an air-supply portion 35 having a compressor, a control circuit and so on. The air-supply portion 35 may either continuously supply the air at constant pressure of which variable setting can be arbitrarily set or send the air like pulses at a frequency of 100 Hz or less, for example (a duty ratio of the pulses can be arbitrarily changed). Such an air blast is performed by an air blast switch provided to an operating portion.

Figures 6A, 6B:
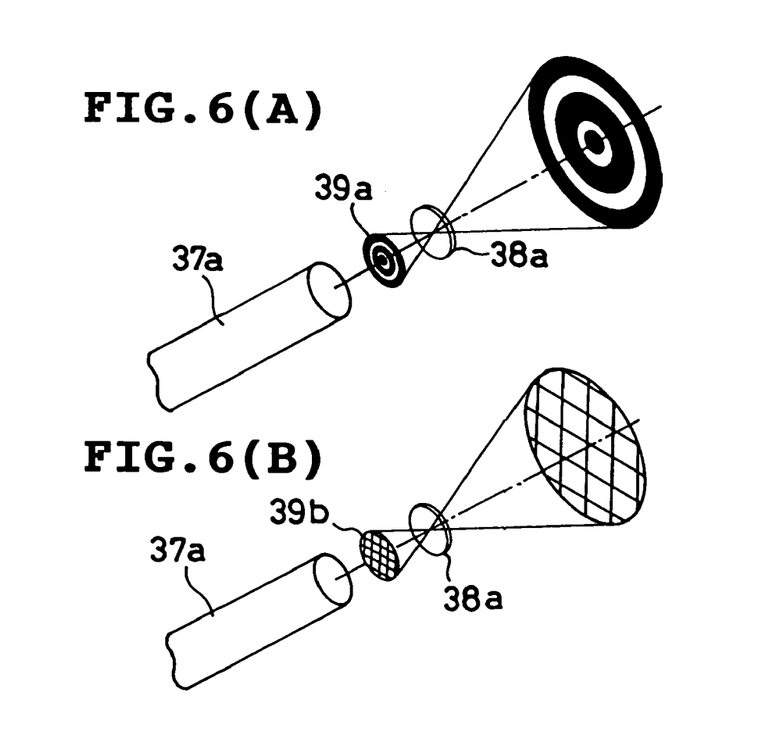
FIG. 6A is a diagram of a concentric pattern and FIG. 6B is a perspective view of a lattice-like pattern.

The endoscope end portion 32 has two light guides 37a and 37b coupled to a light source portion together with illumination windows 38a and 38b placed thereon. One of the light guides 37a has a pattern optical plate 39 inserted between it and the illumination window 38a. As shown in FIGS. 6A and 6B, an optical plate 39a for generating a concentric form pattern and an optical plate 39b for generating a lattice-like form pattern may be used as the pattern optical plate 39. Furthermore, the endoscope end portion 32 has a CCD 42 which is an imaging device provided thereon via an objective optical system 41. The CCD 42 has a signal processing portion 44 and a monitor 45 connected thereto via a signal line (including a power wire) 43.

According to such a second embodiment, the air supplied from the air-supply portion 35 is blasted from the nozzle 34 via the air-pipe 33 based on operation of the air blast switch. And the form patterns in FIG. 6 are projected on an observed object which is the measured object from the light guides 37a via the pattern optical plate 39. The observed object deformed by the air blast and having the form patterns projected thereon is imaged by the CCD 42. An imaging signal of the CCD 42 undergoes various signal processing at the signal processing portion 44, and is then supplied to the monitor 45 on which the image of the observed object having the form patterns projected thereon will be displayed.

Figure 7A:
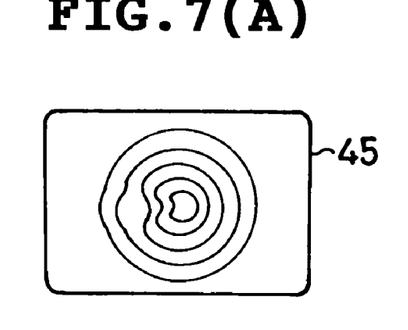
FIG. 7A is a diagram of the concentric pattern and FIG. 7B is a diagram of the lattice-like pattern.
Figure 7B:
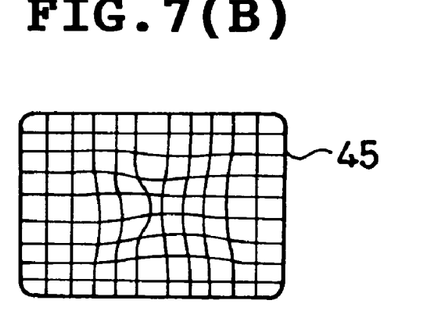

FIG. 7 show the changes of the form patterns projected on the observed object of the surface portion of the same fabric as the measured object 15 shown in FIG. 1, where FIG. 7A is the case of using the concentric pattern optical plate 39a and FIG. 7B is the case of using the lattice-like pattern optical plate 39b. As shown in FIG. 7A, in the case of projecting the concentric pattern, the left side of the concentric circles get distorted as in the case in FIG. 1. And as shown in FIG. 7B, in the case of projecting the lattice-like pattern, the distortion on the left side becomes larger than the right side. Thus, it is possible to visually determine and grasp the hardness distribution from such distortion forms. To be more specific, the hardness can be estimated from concavity and convexity of a measured portion only from the image of the observed object. It is possible, however, to grasp the hardness distribution more correctly and quantitatively by projecting the form pattern. It is possible, by comparing the images in both the cases of performing the air blast and performing no air blast, to more correctly grasp and observe the hardness distribution by means of the form pattern.

According to the second embodiment, it is possible to provide vibrated air to the observed object and display the image synchronous with this aerial vibration. To be more specific, it is feasible, for instance, to form a pulse signal of the frequency of 100 Hz or less at a control portion of the air-supply portion 35 and supply the air of predetermined pressure based on the pulse signal so as to provide the vibrant air to the observed object. And the picture signal formed by an output signal of the CCD 42 is also synchronized with the frequency of the pulse signal and extracted by the signal processing portion 44 so that the image of the observed object is displayed on the monitor 45. In this case, a portion resonating with an oscillation frequency (a normal fabric for instance) and a portion not resonating therewith (a fabric including a hard portion for instance) appear in the image, and a difference between a portion resonating and being deformed and a deformed portion not resonating including an immovable portion appears as distortion of the form pattern. Therefore, it is thereby possible to grasp and observe the hardness distribution.

Third Embodiment

Figure 8:
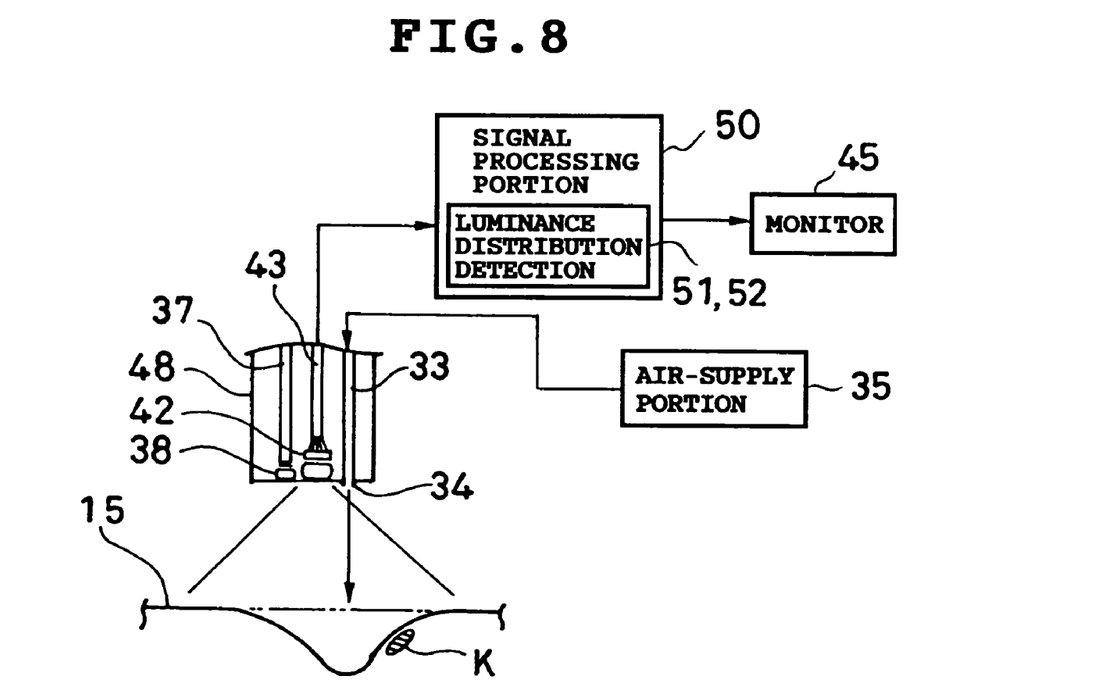
FIG. 8 is a diagram showing the configuration of the surface hardness distribution measuring apparatus for the endoscope according to a third embodiment.

FIG. 8 shows the configuration of a third embodiment (endoscope apparatus) which detects the luminance distribution of the observed object and conspicuously represents the hardness distribution. The basic configuration of an endoscope end portion 48 of the third embodiment is the same as FIG. 5. However, there is no need, as shown in FIG. 8, to place the pattern optical plate between the light guides 37 and the illumination window 38. A luminance distribution detecting circuit 51 is provided in a signal processing portion 50 connected to the CCD 42 by a signal line 43. The luminance distribution detecting circuit 51 compares image luminance in the case of providing no air blast and that in the case of providing the air blast so as to detect changed luminance distribution. For instance, like indication of contours, a plurality of luminance distributions of the same value are obtained at predetermined spacing, and the signal processing portion 50 indicates these luminance distributions like contours.

Figure 9A:
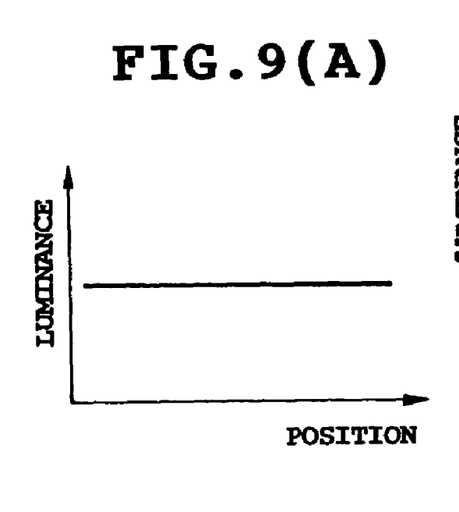
FIG. 9A is a diagram of luminance values before an air blast.
Figure 9B:
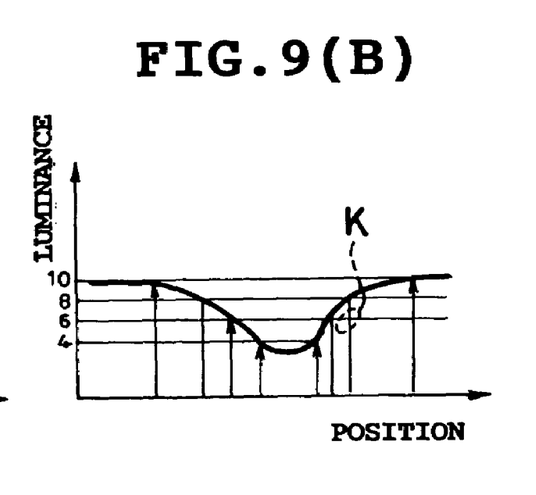
FIG. 9B is a diagram of the luminance values after the air blast and FIG. 9C is a luminance distribution diagram after the air blast.
Figure 9C:
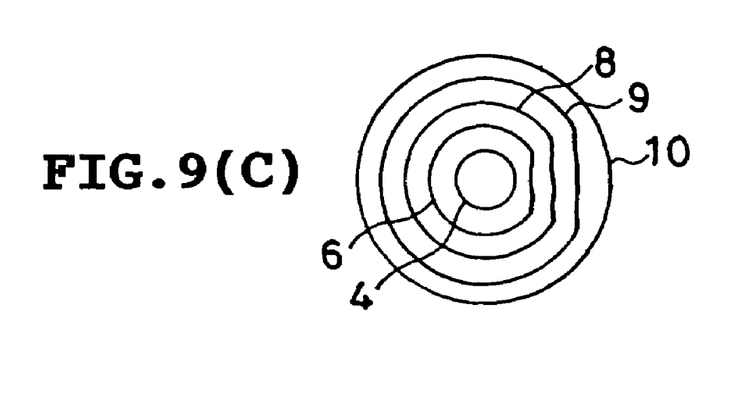

FIG. 9 show the detection and processing of the luminance distribution. For instance, intensity distribution exists in the illumination light via the light guides 37. When a process for rendering the intensity distribution constant is performed, the luminance of the picture signal on the observed object's surface which becomes a plane is constant as shown in FIG. 9A. In the case where the air is blasted via the air-pipe 33 and nozzle 34, the luminance value lowers correspondingly to the amount by which the observed object's surface caves in as in FIG. 9B. To be more specific, the longer the distance is, the weaker the illumination light becomes so that the luminance of the picture signal lowers. Such a change in the luminance (luminance signal) is detected in the luminance distribution detecting circuit 51 so that, for instance, contour indication of the luminance values as shown in FIG. 9C can be obtained by acquiring the luminance distribution of the luminance values 4, 6, 8, 9 and 10 when representing the luminance in ten stages. This contour indication is displayed by being superposed on the image of the observed object. If the hardness is even at the pressed concavity, the contour indication of the luminance becomes a concentric pattern. In the case where a hard portion K exists and is elevated on the right side as in FIG. 9B, the form of the circle on the right side gets distorted as in FIG. 9C so that the hardness of the observed object can be visually determined.

Fourth Embodiment

Figure 10A:
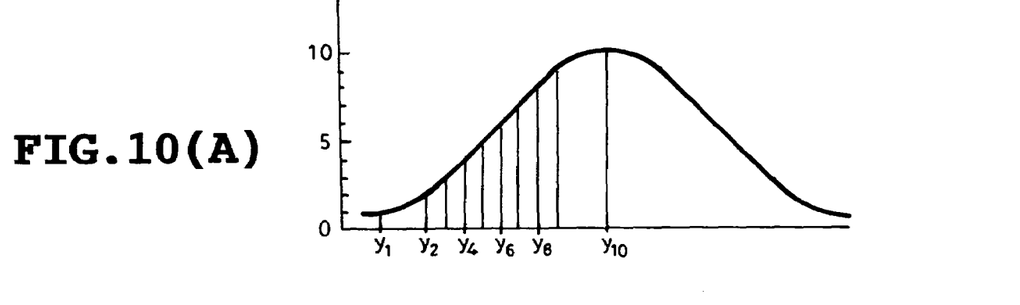
FIG. 10A is a luminance distribution diagram on irradiating illumination light on a plane.
Figure 10B:
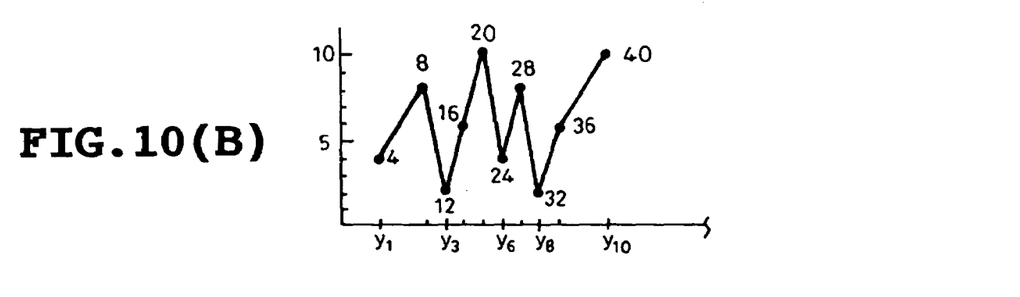
FIG. 10B is a diagram of the values on multiplying the luminance values in FIG. 10A by a predetermined coefficient (4) and FIG. 10C is a luminance distribution diagram.
Figure 10C:
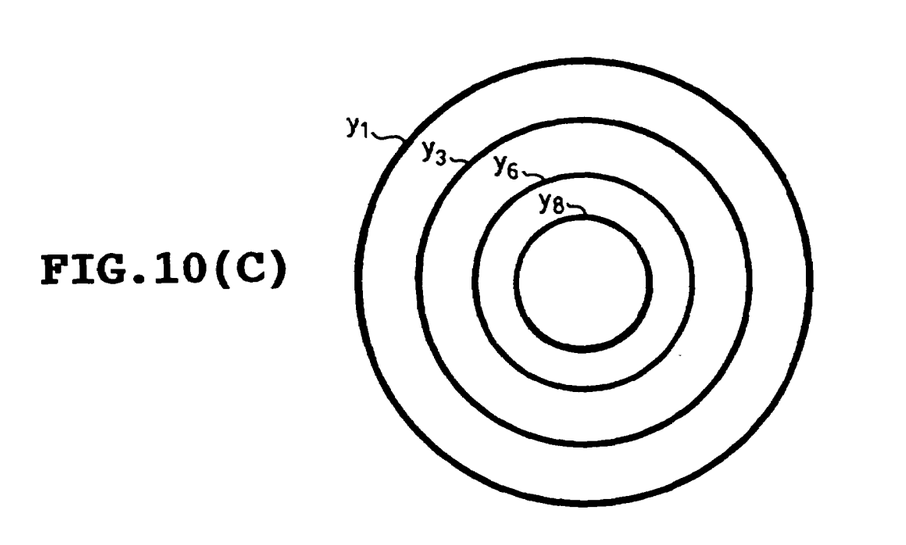

FIG. 10 show the configuration of a fourth embodiment (endoscope apparatus) for performing the process different from the third embodiment in order to detect the luminance distribution of the observed object and display the hardness distribution. The configuration of the endoscope apparatus of the fourth embodiment is the same as FIG. 8. And a luminance distribution detecting circuit 52 (FIG. 8) of the fourth embodiment multiplies a digital luminance signal of the picture signal for instance by a large coefficient exceeding a maximum luminance value so as to represent the luminance distribution in the concentric pattern.

To be more specific, the illumination light irradiated from the illumination window 38 has the intensity distribution as shown in FIG. 10A. If the illumination light is given to the observed object's surface which becomes the plane, the image of the same luminance distribution can be obtained. Consideration is given to the case of representing the luminance distribution in ten stages (a 256-step gradation in 8-bit configuration or a like gradation in reality) and overflowing if this luminance value 10 is exceeded. For instance, if multiplied by a coefficient 4, luminance 1 is 4 ($y_1$), 2 is 8 ($y_2$), 3 is 12 ($y_3$), 4 is 16 ($y_4$), 5 is 20 ($y_5$), 6 is 24 ($y_6$), . . . 10 is 40 ($y_{10}$), and $y_3$, $y_6$ and $y_8$ become 2 ($y_3$), 4 ($y_6$) and 2 ($y_8$) due to overflow, as shown in FIG. 10B.

Therefore, if multiplied by the coefficient which makes the luminance overflow, the luminance extremely lowers at $y_3$, $y_6$ and $Y_8$ so that the luminance distribution in the concentric pattern as in FIG. 10C appears. Such luminance distribution becomes the concentric pattern in FIG. 1C in the case of a flat surface or a concavity having an even gradient. In the case of an uneven surface, however, the distortion arises to the concentric pattern as in FIG. 9C. The luminance distribution in the concentric pattern is displayed on the monitor 45 by superposing it on the image of the observed object so that it is possible to visually grasp and observe the hardness of the surface portion of the observed object according to a degree of the distortion of the pattern.

It is preferable, as to detection of the luminance distribution according to the third and fourth embodiments, to measure the hardness distribution before providing the air blast in addition to that on providing the air blast. To be more specific, the surface of the observed object is not necessarily the plane but often has the concavities and convexities, and so it can be grasped correctly by comparing the images of the hardness distribution before and after the air blast. It is also feasible, in the luminance distribution detecting process in the luminance distribution detecting circuits 51 and 52, to acquire the change, that is, the difference in the luminance of the image of the observed object between before and after the air blast and detect the luminance distribution of the image of the difference in the luminance so as to display a pattern representing the hardness distribution.

As for the measurement of the surface hardness distribution with the endoscope according to the second to fourth embodiments, the observed object is not completely fixed so that the entire observed object moves a little due to the air blast to detect and grasp relative hardness. When measuring a farm product and so on, however, it is possible to measure an absolute value of the hardness by fixing the measured object. To be more specific, it is possible, by keeping a fixed distance between an air blast portion and the measured object, to set up a condition for giving constant pressure to the measured object so as to detect the absolute value of the hardness by means of an amount of concavity (caving) deformed by the air blast.

Figure 11A:
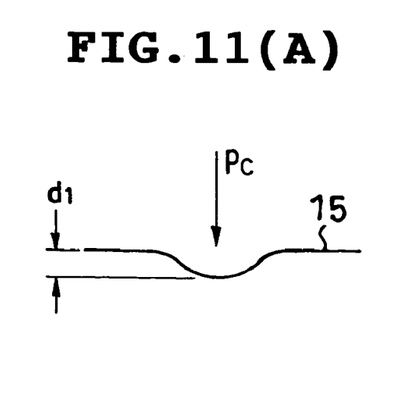
FIGS. 11A and 11B are diagrams for explaining measurement of absolute values of hardness in the embodiment.
Figure 11B:
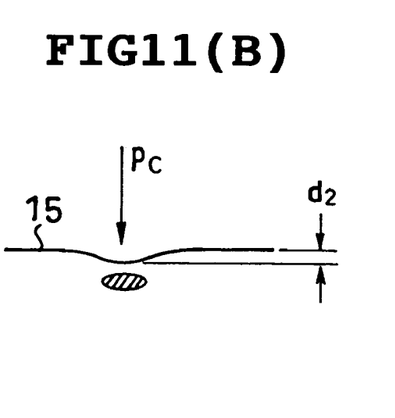

For instance, as shown in FIG. 11, when the air blast of constant pressure Pc is given to the measured object 15 and the amount of concavity thereof is detected by the line laser sensor 23 of the second embodiment, an amount of concavity $d_1$ as in FIG. 11A is measured in the case of a soft measured object. As opposed to it, an amount of concavity $d_2$ smaller than $d_1$ as in FIG. 11B is measured in the case of a hard measured object. It is possible to detect the absolute value of the hardness by means of the values $d_1$ and $d_2$. It is also possible to evaluate the hardness by estimating the impedance parameter based on the above-mentioned formula 2.

As for the air blast according to the third and fourth embodiments, it is also feasible to supply the air like pulses at the predetermined oscillation frequency in addition to continuously supplying the air at constant pressure of which variable setting can be arbitrarily set as described in the second embodiment. While the cases of blasting the air were described as to the embodiments, it is also possible to spray another medium such as liquid or apply pressing force with a stick and so on.

Figure 12:
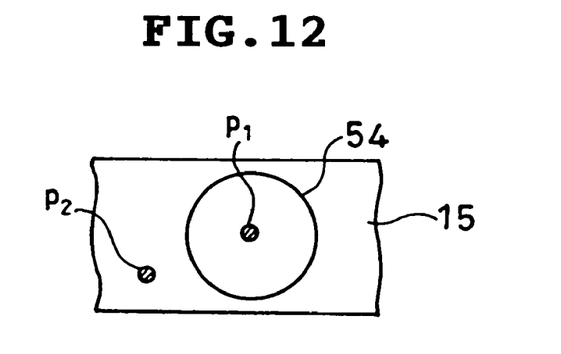
FIG. 12 is a diagram showing points to which the air blast is given in the embodiment.

FIG. 12 shows points for exerting the pressing force with the air blast and so on in all the above embodiments, where the pressing force may be exerted on a position $p_2$ outside an imaging range 54 of the measured object 15 in addition to the case of exerting it on a central position $p_1$ of the imaging range 54 or the proximity thereof.

The present invention may be applied to the measurement of the hardness distribution of the farm product (surface portion) such as a vegetable or a fruit and relative hardness distribution of an observed area (surface portion) in a medical field or the measurement of the hardness distribution of various substances (surface portion) in other fields.

What is claimed is:

1. A surface hardness distribution measuring method, including:
    a pressing step of exerting a force on a surface portion of a measured object by pressing with a blast of air; and
    a hardness distribution representing step of providing a visual representation of hardness distribution of the measured object on exerting the force in the pressing step.

2. A surface hardness distribution measuring apparatus comprising:
    pressing means for exerting a pressing force on a surface portion of a measured object;
    apparatus for performing visual representation of surface hardness distribution of the measured object on exerting the pressing force with the pressing means; and
    a display for visually representing the hardness distribution;
    further comprising a projector for projecting a form pattern on the measured object as the hardness distribution representing apparatus, and
    a CCD for observing the measured object which has the form pattern projected thereon by the projector and the force exerted thereon by the pressing means, and
    wherein the display displays an image of the measured object observed by the CCD.

3. The surface hardness distribution measuring apparatus according to claim 2, wherein the projector projects a concentric pattern.

4. The surface hardness distribution measuring apparatus according to claim 2, wherein the projector projects a lattice-like pattern.

5. The surface hardness distribution measuring apparatus according to claim 2, wherein the pressing means blasts air on a surface of the measured object.

6. The surface hardness distribution measuring apparatus comprising:
    pressing means for exerting a pressing force on a surface portion of a measured object;
    apparatus for performing visual representation of surface hardness distribution of the measured object on exerting the pressing force with the pressing means; and
    a display for visually representing the hardness distribution;
    further comprising:
    a CCD for observing the measured object on which the pressing force is exerted;
    a luminance distribution detecting circuit, for detecting luminance distribution of the measured object image obtained by the CCD; and
    wherein the display displays the luminance distribution obtained by the luminance distribution detecting circuit.

7. The surface hardness distribution measuring apparatus according to claim 6, wherein the pressing means blasts air on a surface of the measured object.

8. The surface hardness distribution measuring apparatus according to claim 6, wherein the luminance distribution detecting circuit detects luminance distribution of images according to predetermined spacing in order to display contours of luminance, and the display displays the contours of luminance superimposed on an image of the observed object.

9. The surface hardness distribution measuring apparatus according to claim 6,
    wherein the luminance distribution detecting circuit multiplies a luminance signal of the image by a large coefficient exceeding a maximum luminance value to display the contours of luminance, and
    the display portion displays the contours of luminance superimposed on an image of the observed object.

10. A surface hardness distribution measuring apparatus, comprising:
    an air blast for exerting a pressing force on a surface portion of a measured object;
    a line laser for detecting the hardness distribution of the measured object in one or more dimensions on exerting the pressing force with the air blast; and
    a display for displaying the hardness distribution in one or more dimensions.

* * * * *